United States Patent [19]

Muttitt

[11] Patent Number: 4,721,111
[45] Date of Patent: Jan. 26, 1988

[54] MEDICAL ELECTRODE AND METHOD OF MAKING THE ELECTRODE

[75] Inventor: Raymond I. Muttitt, Norwich, England

[73] Assignee: Sciotronic Limited, Newmarket, England

[21] Appl. No.: 830,585

[22] PCT Filed: Jun. 6, 1985

[86] PCT No.: PCT/GB85/00241
§ 371 Date: Feb. 5, 1986
§ 102(e) Date: Feb. 5, 1986

[87] PCT Pub. No.: WO86/00008
PCT Pub. Date: Jan. 3, 1986

[30] Foreign Application Priority Data

Jun. 8, 1984 [GB] United Kingdom ............... 8414673

[51] Int. Cl.$^4$ ............... A61B 5/04; H01R 43/00
[52] U.S. Cl. ................................. 128/640; 29/877
[58] Field of Search ................. 128/634–641, 128/643, 644, 798, 802, 803; 29/825, 877

[56] References Cited

U.S. PATENT DOCUMENTS

| | | | |
|---|---|---|---|
| 2,872,926 | 2/1959 | Alderman | 128/640 |
| 3,340,868 | 9/1967 | Darling | 128/640 |
| 3,581,736 | 6/1971 | Zenkich | 128/641 |
| 3,587,565 | 6/1971 | Tatoian | 128/640 |
| 4,016,869 | 4/1977 | Reichenberger | 128/640 |
| 4,082,086 | 4/1978 | Page et al. | 128/641 |
| 4,327,737 | 5/1982 | Szpur | 128/640 |
| 4,362,165 | 12/1982 | Carmon et al. | 128/640 |
| 4,393,584 | 7/1983 | Bare et al. | 128/877 |
| 4,409,981 | 10/1983 | Lundberg | 128/640 |
| 4,441,500 | 4/1984 | Sessusno et al. | 128/641 |

FOREIGN PATENT DOCUMENTS 1402205 8/1975 United Kingdom ............... 128/640

Primary Examiner—Lee S. Cohen
Attorney, Agent, or Firm—Shoemaker and Mattare, Ltd.

[57] ABSTRACT

A medical electrode comprises a support (10) coated on each face with an adhesive and formed with a through hole. A conductive gel pad (14) is adhered to a first face of the support (10) beneath the through hole and a contact pad (12) of inert electrically conductive liquid impervious material such as silver is adhered to the first face of the support (10) between the support (10) and the gel pad (14) beneath the through hole. A connector (16) is adhered to the second face of the support, is electrically connected through the through hole to the contact pad (12), and leads from the contact pad (12) to the edge of the electrode. A method of making the electrode is also disclosed.

8 Claims, 4 Drawing Figures

MEDICAL ELECTRODE AND METHOD OF MAKING THE ELECTRODE

FIELD OF THE INVENTION

The present invention relates to a medical electrode and to a method for making it.

BACKGROUND OF THE INVENTION

Disposable medical electrodes are used in cardiac monitoring by ECG. A disposable medical electrode for deriving electrical signals from a patient's skin is described in U.S. Pat. No. 3,977,392 (Eastprint Inc). The Eastprint electrode is intended to conform to the contour of the patient's body and to provide a good conductive path between a skin area underlying the electrode and an electrical contact in the form of a male snap fastener element projecting from the top of the electrode. A support layer in the form of a soft compliant layer of polyurethane foam has an aperture in which a gel pad is a compression fit. The lower face of the support layer is adhesive coated. The contact element and the foil strip are offset on the support layer with a flexible conductive foil strip connecting them so that movement of the contact element does not disturb the conductive path between that element and the skin area to which the electrode is adhered. The foil strip both makes the contact with the gel pad and provides the connection to the remotely located contact element, and for the former purpose it has to be unattacked by the gel material and to be electrically compatible with the gel pad, and so silver or other relatively expensive materials have to be used. Furthermore the Eastprint electrode is complex and inherently expensive to make, so that it would not be attractive for use in routine diagnostic procedures.

Recently 3M Health Care have introduced the so-called Littman diagnostic ECG electrode which uses a solid gel electrolyte on the lower face of aluminium foil. But a solid gel presents problems where it is necessary to make contact through the skin on a hairy chest, and requires a 20–30 second delay before the skin is penetrated and contact is established.

SUMMARY OF THE INVENTION

It is an object of the invention to provide a disposable ECG electrode that can provide an electrical signal comparable with the best existing electrodes, but which employs a conventional soft gel for rapid penetration of the skin's horny outer layer and which can be made very inexpensively.

The invention is based on the realisation that if the support is an impermeable material the contact pad can be located on the lower or concealed face of the support and can be contacted through the support, in which case it performs the dual function of making the contact with the gel pad and physically separating the gel pad from a connector on the top or exposed face.

The invention therefore provides a medical electrode comprising:

(a) a support coated on each face with an adhesive and formed with a through hole;

(b) a conductive gel pad adhered to a first face of the support beneath the through hole;

(c) a contact pad of inert electrically conductive liquid impervious, material adhered to the first face of the support between the support and the gel pad beneath the through holes; and (d) a connector adhered to the second face of the support, electrically connected through the through hole to the contact pad, and leading from the contact pad to the edge of the electrode.

The invention further provides a method for making a medical electrode which comprises:

forming apertures in a strip of support material coated on its first and second faces with an adhesive;

adhering a connector to the second face of the support, said connector extending from the through hole to the edge of the support;

covering the second face and the connector with a protective plastics film coextensive with the support;

adhering an electrode contact pad of an inert metal foil to the first face of the support so as to underlie the through-hole;

adhering a conductive gel pad to the first face of the support so as to underlie and surround the contact pad; and impregnating the pad with conductive gel.

DESCRIPTION OF PREFERRED FEATURES

Preferably a protective liquid-impermeable plastics film at least coextensive with the support and domed to receive the contact pad is attached to the first face of the support and a protective plastics film coextensive with the support and overlying the connector is adhered to the second face of the support.

BRIEF DESCRIPTION OF THE DRAWINGS

An embodiment of the invention will now be described with reference to the accompanying drawings, in which.

DETAILED DESCRIPTION OF PREFERRED EMBODIMENT

Figure 1:
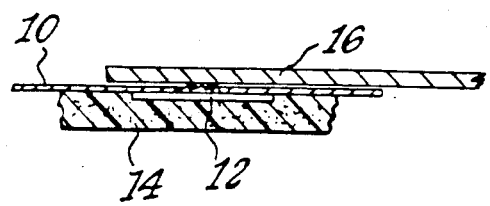
FIG. 1 is a section through a patient electrode according to the invention.

In the drawings, a support 10 for the electrode is provided by a piece of double-sided adhesive plastics tape formed in its middle with a small through hole. Adhered beneath the hole is a contact pad 12 which may be a small square or disc of silver. The contact pad 12 is adhered all around the hole and thereby prevents liquid passing therethrough. On the lower face of the support 10 and surrounding the contact pad 12 is adhered a disc 14 of plastics sponge material impregnated with a conductive gel. On the outer face of the support 10 is adhered a connector in the form of a strip 16 of brass or other suitable material that extends from an edge of the support 10 to the through hole, where it is soldered or welded to the contact pad 12. It will be appreciated that the support 10 provides the two functions of acting as an insulator and acting as a barrier to prevent contact between the brass or tin contact strip 16 and the gel in the pad 14. The silver contact pad 12 may be used in association with a gel containing chloride ions, and the contact pad may have deposited thereon or formed in situ a film of silver chloride. The couple Ag/AgCl gives a very low contact potential. The upper face of the support 10 may be covered with a plastics cover strip. The lower face of the electrode is covered with a release coated film 18 of PVC or other suitable plastics material coated with silicone as release agent. The film 18 may be formed by means of a heated tool to define a dome 20 into which the pad 14 on the lower face of the electrode fits.

Figure 2:
FIG. 2 is a section of a protective cover strip for releaseable attachment to the electrode of FIG. 1.
Figure 3:
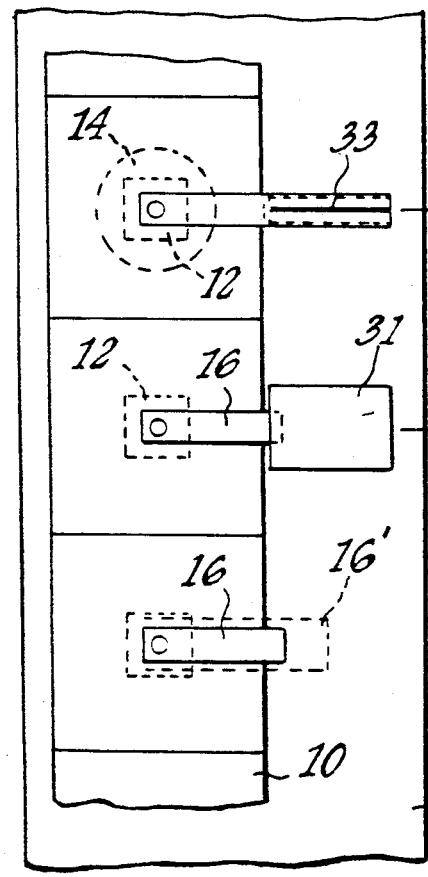
FIG. 3 is a diagram showing successive stages in a process for manufacturing the electrode of FIG. 1.
Figure 4:
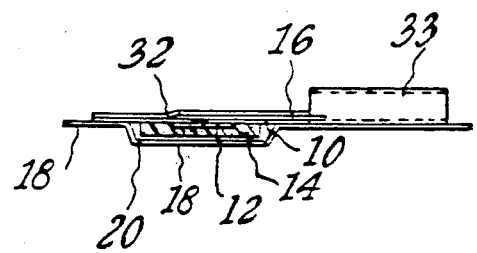
FIG. 4 is a section of a complete electrode.

FIG. 3 shows three separate forming stations in a process for forming a patient electrode of the kind described with reference to FIGS. 1 and 2. The support 10 is carried on a strip of protective release paper that is advanced in indexed steps by drive means (not shown) and holes are formed therein by means of a hole puncher. The face of the support 10 that becomes the upper face of the electrode is initially exposed with the support inverted from the attitude on the patient, and the connector 16 is cut from brass strip and is adhered thereto from underneath. A slightly larger piece of brass strip is cut to define a blank for a contact bush 31 that is welded to the tip of the connector 16. A film of PVC 32 coextensive with the electrode support 10 is then rolled onto the exposed upper surface of the support 10, and the bush blank 31 is covered with adhesive tape. A forming machine then folds the bush blank 31 into a hollow bush 33, after which the release paper is removed from the top face of the support 10. The piece of silver 12 is then severed from strip and placed on the support from above, after which the connector 16 and the contact pad 12 are soldered or otherwise conductively joined together. The sponge pad 14 is then cut to size and placed on top of the silver contact pad 12 and adhesive, after which the conductive gel is squeezed into the sponge pad 14. The protective PVC film 18 which is coextensive with the electrode support 10 is then placed downwards onto the lower or working face of the support 10 with the pad 14 in the dome 20 and the two are pressed together, after which cuts in the support 10 are made between individual electrodes and the film 18 is cut to define strips of conveniently five or ten electrodes.

It will be appreciated that various modifications may be made to the embodiment described above without departing from the invention, the scope of which s defined in the appended claims. For example, the electrodes could have a simple clamp connection instead of a bush connection, in which case the contact strip 16' (FIG. 3) is slightly larger and extends further beyond the edge of the electrode. Alternatively, they could have snap connectors.

I claim:

1. A medical electrode comprising:
    a support of double-sided liquid-impermeable plastics adhesive tape having two faces and formed with a through-hole;
    an electrode plate of metal foil liquid-tightly adhered to a first face of the support to cover the through hole;
    a connector of metal strip adhered to face-to-face contact with the second face of the support, electrically connected through the through-hole to the electrode plate and having a free end extending beyond an edge of the support;
    a protective plastics film coextensive with the support adhered to the second face of the support so as to overlie the connector strip;
    a contact pad of open-celled plastics foam adhered to the first face of the support beneath and in electrical contact with the electrode plate and impregnated with a conductive gal; and
    a protective liquid-impermeable plastics film at least coextensive with the support and attached to the first face thereof, a dome formed in said film acting as a container for the pad.

2. An electrode according to claim 1, wherein the electrode plate is of silver.

3. An electrode according to claim 2, wherein the connector is a brass strip.

4. An electrode according to claim 3, wherein a contact bush is attached to the free end of the connector strip.

5. A method for forming medical electrodes which comprises:
    forming apertures in a strip of double-sided plastics tape coated on its first and second faces with an adhesive;
    adhering connectors to the second face of the plastics tape at intervals corresponding to the spacing of the apertures to an edge of the plastics tape;
    covering the second face and connectors with a protective plastics film coextensive with the plastics tape;
    adhering contact pads of inert material to the first face of the plastics tape at intervals corresponding to the spacing of the apertures so that each contact pad underlies a respective aperture, covers the respective aperture and electrically connects to a respective connector;
    adhering conductive gel pads to the first face of the plastics tape at intervals corresponding to the spacing of the apertures so that each gel pad underlies and surrounds a respective contact pad; and
    impregnating the gel pads with conductive gel.

6. A method according to claim 5, further comprising the steps of forming domes in a strip of release coated protective plastics film material at intervals corresponding to the spacing of the apertures and adhering the protective film material to the first face of the plastics tape with the gel pads received in respective domes.

7. A method according to claim 6 comprising severing the plastics tape, the release coated plastics film and the protective plastics film at locations between said apertures to form separated electrodes as defined by the lines of severance.

8. A method according to claim 5, wherein bush blanks are fastened directly to respective connectors and folded to form bushes.

* * * * *